United States Patent
Kim et al.

(10) Patent No.: US 6,607,867 B1
(45) Date of Patent: Aug. 19, 2003

(54) ORGANOMETAL-CONTAINING NORBORNENE MONOMER, PHOTORESIST CONTAINING ITS POLYMER, MANUFACTURING METHOD THEREOF, AND METHOD OF FORMING PHOTORESIST PATTERNS

(75) Inventors: Jin-Baek Kim, Seoul (KR); Jae-Jun Lee, Jinju-shi (KR); Jae-Sung Kang, Taejon (KR)

(73) Assignee: Korea Advanced Institute of Science and Technology, Taejon (KR)

( * ) Notice: Subject to any disclaimer, the term of this patent is extended or adjusted under 35 U.S.C. 154(b) by 118 days.

(21) Appl. No.: 09/790,632

(22) Filed: Feb. 23, 2001

(30) Foreign Application Priority Data

Jun. 30, 2000 (KR) .......................................... 2000-37060

(51) Int. Cl.$^7$ .......................... G03F 7/004; C07C 69/74; G03C 5/00
(52) U.S. Cl. ..................... 430/270.1; 430/905; 430/323; 560/120; 556/465; 526/281
(58) Field of Search ................................ 526/281, 282; 430/270.1, 905, 326, 323; 560/120; 556/465

(56) References Cited

U.S. PATENT DOCUMENTS

| | | | |
|---|---|---|---|
| 6,103,445 A | | 8/2000 | Willson et al. .......... 430/270.1 |
| 6,444,408 B1 | * | 9/2002 | Brock et al. ................ 430/322 |

OTHER PUBLICATIONS

Chemical Aspects of Silicon–Containing Bilayer Resists, Boardman, L.D. et al. SPIE, vol. 3678, pt. 1, 1999, 562–572.*
SPIE's 25$^{th}$ Annual International Symposium on Microlithography—Part of SPIE's Thematic Applied Science and Engineering Series, Feb. 27–Mar. 3, 2000, "Emerging Lithographic Technologies Metrology, Inspection, and Process Control Resist Technology and Processing Optical Microlithography".

* cited by examiner

*Primary Examiner*—Rosemary Ashton
(74) *Attorney, Agent, or Firm*—Foley & Lardner (57) ABSTRACT

The present invention relates to norbornene monomers with a novel functional group containing an organometal as shown in the following Formula (I) or (II), a photoresist containing its polymers, manufacturing method thereof, and a method of forming photoresist patterns.

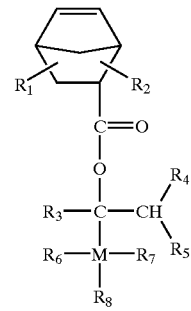

(I)

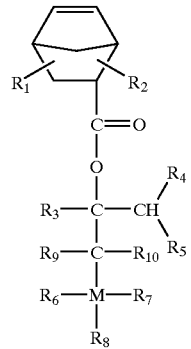

(II)

Unlike existing polymers for photoresist matrix, polymers made by norbornene monomers described in the present invention is a chemical amplification type induced by photosensitive acids and can result in difference in silicon content between the exposed area and unexposed area due to dissociation of side chain containing silicon. The difference in the silicon content results in different etch rate with respect to oxygen plasma which makes dry developing possible.

8 Claims, 8 Drawing Sheets

ORGANOMETAL-CONTAINING NORBORNENE MONOMER, PHOTORESIST CONTAINING ITS POLYMER, MANUFACTURING METHOD THEREOF, AND METHOD OF FORMING PHOTORESIST PATTERNS

BACKGROUND OF THE INVENTION

1. Field of the Invention

The present invention relates to norbornene monomers containing an organometal and its manufacturing method, especially to norbornene monomers with a novel functional group containing an organometal used for the manufacturing of a photoresist, and its manufacturing method.

Furthermore, the present invention relates to photoresist and its manufacturing method, especially to phtoresist which can form high resolution patterns in deep-UV wavelength region by copolymerizing aforementioned norbornene monomers or by copolymerizing norbornene monomers with other material, and its manufacturing method.

Still furthermore, the present invention relates to a method forming the aforementioned phtoresist patterns.

2. Description of the Prior Art

With increasing integration of semiconductor devices, there may be a heightened need to form finer patterns of subquarter micron in photolithographic processes. According to the request of fine patterns, processes that can form patterns utilizing deep-UV light from KrF eximer laser with wavelength of 248 nm or ArF eximer laser with wavelength of 193 nm which have shorter wavelength than existing g-line with wavelength of 436 nm or I-line with wavelength of 365 nm came to be necessary.

The photoresist containing Novolac-naphtoquinonediazide compounds utilized in the g-line and I-line has strong absorption in the deep-UV region and is low in sensitivity that it can not be applied in the deep-UV wavelength region. Therefore, the development of new photoresist is required.

New photoresist should satisfy various requirements such as high sensitivity, contrast, high resolution, and resistance to dry etching process. Among them, the sensitivity is the most important in the development of photoresist and the concept of chemical amplification is introduced to enhance sensitivity.

The chemically amplified photoresist is comprised of photosensitive acid generator (PAG) and a polymer combined with dissolution inhibitor.

The exposure of the chemically amplified photoresist hydrolyzes dissolution inhibitor on a polymer main chain by the catalytic reaction of acid from photosensitive acid generator, and the polarity of polymer is changed. Its development in polar or nonpolar solvent yields positive or negative type photoresist patterns. U.S. Pat. No. 4,991,628 discloses the use of polyvinylphenol protected by t-butoxycarbonyl functional group for the application in the chemically amplified photoresist.

However, both the conventional positive or negative type chemically amplified photoresists have several problems. Major problems are deformation and collapse of resist pattern in a wet developing and rinsing according to the increase of aspect ratio of a pattern.

To overcome the problems, the strength of matrix polymer contained in photoresist and the adhesion of photoresist to substrate must be good and appropriate developing and rinsing solution should be selected. However, the solution has also limits because the increase of aspect ratio is inevitable and adhesion has limit, too.

SUMMARY OF THE INVENTION

Therefore, the first object of the present invention is to provide norbornene monomers containing novel organometal for the manufacuture of photoresist, which can form high resolution patterns in deep-UV wavelength region.

The second object of the present invention is to provide a norbornene monomer manufacturing method containing appropriate organometal to achieve the above described object.

The third object of the present invention is to provide photoresist utilizing norbornene monomers supplied by achieving the first object.

The fourth object of the present invention is to provide a photoresist manufacturing method suitable to achieve the third object.

The fifth object of the present invention is to provide a method for forming patterns of photoresist, which is supplied by achieving the third object.

Norbornene monomer containing organometal for photoresist according to one embodiment of the present invention to achieve the above first object is presented in the following Formula (I), wherein $R_1$ to $R_8$ independently represent hydrogen, alkyls having from 1 to 4 carbon atoms, alkoxy having from 1 to 4 carbon atoms, phenyl or —$MR'_3$; M is either Si, Ge, Sn or OSi; and R' is either alkyl having from 1 to 4 carbon atoms, alkoxy having from 1 to 4 carbon atoms, phenyl, benzyl or phenoxy.

Norbornene monomer containing organometal for photoresist according to another embodiment of the present invention to achieve the above first object is presented in the following Formula (II), (II)

wherein $R_1$ to $R_{10}$ independently represent hydrogen, alkyls having from 1 to 4 carbon atoms, alkoxy having from 1 to 4 carbon atoms, phenyl —$MR'_3$; M is either Si, Ge, Sn or OSi; and R' is either alkyl having from 1 to 4 carbon atoms, alkoxy having from 1 to 4 carbon atoms, phenyl, benzyl or phenoxy.

The norbornene monomer manufacturing method according to one embodiment of the present invention to achieve the above second object is characterized as follows; Alcohol containing organometal as shown in the Formula (XII) or (XIII) is synthesized. The alcohol is reacted with 2-chlorocarbonyl-5-norbornene derivative at 0° C. at ambient atmosphere for 1~2 hours, and then further reacted at room temperature and ambient atmosphere for 5~6 hours to yield norbornene monomer as shown in Formula (I) or (II). The synthetic methods for alcohol with Formula (XII) or (XIII) are reported previously (J. Organomet. Chem. 49(1973) C9-C12, J. Org. Chem 45(1980) 3571–3578, Tetrahedron Lett. (1976) 1591–1594, J. Organomet. Chem. (1981) 33–47), wherein $R_1$ to $R_{10}$ independently represent hydrogen, alkyls having from 1 to 4 carbon atoms, alkoxy having from 1 to 4 carbon atoms, phenyl or —$MR'_3$; M is either Si, Ge, Sn or OSi; and R' is either alkyl having from 1 to 4 carbon atoms, alkoxy having from 1 to 4 carbon atoms, phenyl, benzyl or phenoxy.

The photoresist according to one embodiment of the present invention to achieve the above third object is characterized to comprise a polymer and a photosensitive acid generator as shown in the following Formula (III),

(III)

wherein $R_1$ to $R_8$ independently represent hydrogen, alkyls having from 1 to 4 carbon atoms, alkoxy having from 1 to 4 carbon atoms, phenyl or —$MR'_3$; M is either Si, Ge, Sn or OSi; and R' is either alkyl having from 1 to 4 carbon atoms, alkoxy having from 1 to 4 carbon atoms, phenyl, benzyl or phenoxy; n is degree of polymerization and is between 1 to 100.

The photoresist according to another embodiment of the present invention to achieve the above third object is characterized to comprise a polymer and a photosensitive acid generator (not shown) as shown in the following Formula (IV),

(IV)

wherein $R_1$ to $R_{10}$ independently represent hydrogen, alkyls having from 1 to 4 carbon atoms, alkoxy having from 1 to 4 carbon atoms, phenyl or —$MR'_3$; M is either Si, Ge, Sn or OSi; and R' is either alkyl having from 1 to 4 carbon atoms, alkoxy having from 1 to 4 carbon atoms, phenyl, benzyl or phenoxy; n is degree of polymerization and is between 1 to 100.

The photoresist according to another embodiment of the present invention to achieve the above third object is characterized to comprise a polymer and a photosensitive acid generator as shown in the following Formula (V), (V)

wherein, A represents the following Formula (VII) or (VIII), and (VII)

(VIII)

wherein $R_1$ to $R_{10}$ independently represent hydrogen, alkyls having from 1 to 4 carbon atoms, alkoxy having from 1 to 4 carbon atoms, phenyl or $-MR'_3$; M is either Si, Ge, Sn or OSi; and R' is either alkyl having from 1 to 4 carbon atoms, alkoxy having from 1 to 4 carbon atoms, phenyl, benzyl or phenoxy; x,y,z are mole ratio of a polymer and x+y+z=1.

The photoresist according to another embodiment of the present invention to achieve the above third object is characterized to comprise a polymer and a photosensitive acid generator as shown in the following Formula (VI), (VI)

wherein A represents the above Formula (VII) or (VIII), and B represents the following Formula (IX), (X))or (XI), and (IX)

(X)

(XI)

wherein $R_1$ to $R_{10}$ independently represent hydrogen, alkyls having from 1 to 4 carbon atoms, alkoxy having from 1 to 4 carbon atoms, phenyl or $-MR'_3$; M is either Si, Ge, Sn or OSi; and R' is either alkyl having from 1 to 4 carbon atoms, alkoxy having from 1 to 4 carbon atoms, phenyl, benzyl or phenoxy. $R_{11}$ to $R_{13}$ independently represent hydrogen or alkyl; x,y,z are mole ratio of a polymer and x+y+z=1.

The photoresist manufacturing method according to one embodiment of the present invention to achieve the above fourth object is characterized to comprise the steps of; manufacturing of norbornene monomers as shown in the above Formula (I) or (II); manufacturing of polymer either polymerizing the norbornenes, copolymerizaing norbornenes with maleic anhydride, or polymerizing in a radical method by mixing silicon-containing acrylate or methacrylate monomer as well as maleic anhydride with norbornene monomers; dissolving the above polymer and photosensitive acid generator in solvent.

Benzoyl peroxide, 2,2'-azobisisobutyronitrile, acetylperoxide, laurylperoxide, or di-t-butylperoxide are used for radical initiators for the polymeriazation. Benzene, toluene, tetrahydrofuran or mixtures of them are used for polymerization solvent. The polymerization is performed at 50~70° C. for 6~30 hours in a flask under nitrogen atmosphere.

Monomers in the above Formula (I) or (II) are polymerized to give a resin for photoresist. However, copolymerization with monomers such as maleic anhydride is desirable to provide better properties such as improved adhesive properties onto substrate or increased glass transition temperature.

On the other hand, as described below one of the characteristics of the present invention is that upon exposure the silicon content of photoresist film is different between the exposed area and unexposed area, which differentiate the etching speed toward oxygen plasma between the exposed area and unexposed area and makes dry developing possible. Therefore, to increase the difference in etching speed, copolymerization of monomers in Formula (I) or (II) with maleic anhydride, silicon-containing acrylate or methacrylate monomers is desirable as explained.

If the aforementioned 'M' is silicon, it is generally desirable to have more than 7% of silicon to have different etching speed between exposed area and unexposed area. The introduced monomer ratio for a difference in etching speed should be controlled in consideration of silicon weight content, glass transition temperature and adhesion.

The photoresist pattern forming method according to one embodiment of the present invention to achieve the above fifth object is characterized to comprise the steps of; forming photoresist film on a substrate by coating photoresist which is provided through the achievement of the above fourth object; exposing the above photoresist film through exposure mask; baking the above exposed product; selective etching of exposed area in the above photoresist film by a reactive ion etching utilizing oxygen plasma.

Irradiation of deep-UV light on the photoresist film coated on the above substrate produces materials described in the Formula (XIV) or (XV).

(XIV)

(XV)

Therefore, in order to remove materials described in the above Formula (XIV) or (XV), baking is followed by the exposure step. The desirable baking condition is at 90~140°

C. for 90~120 seconds. The materials described in the Formula (XIV) or (XV) may have volatility at post exposure baking (PEB) temperature by a suitable modification of $R_3$ to $R_{10}$ groups, and they can also be removed by extraction if not volatile.

The above photoresist film formation includes steps of; dissolving the polymer with 1–10 wt % of photosensitive acid generator such as triphenylsulfonium triflate or other onium salts in propylene glycol monomethyletheracetate or cyclohexanone solvents followed by filtering to manufacture photoresist solution; spin-coating the above solution on a silicon wafer; soft-baking for 90~120 seconds on a hot plate at 90~120° C.

In the area irradiated by deep-UV light, the side chain including silicon(designated by M) containing portion is decomposed by an acid catalysts during post exposure baking (PEB) to yield the above Formula (XIV) or (XV) and is then removed. The area which is not irradiated by deep-UV light is stable at post exposure baking (PEB) temperature and the silicon content is not different from the initial content. Therefore, the post exposure baking (PEB) leaves clear latent image on the surface of photoresist. Upon the etching of latent image by oxygen reactive ion etching, the exposure area is removed by decomposition and the unexposed area is not etched due to the SiOx film on the surface resulting from remained silicon components. It results in photoresist patterns.

BRIEF DESCRIPTION OF THE DRAWINGS

These and other features of the present invention and the attendant advantages will be readily apparent to those having ordinary skill in the art and the invention will be more easily understood from the following detailed description of the preferred embodiments of the present invention taken in conjunction with the accompanying drawings wherein.

DESCRIPTION OF THE PREFERRED EMBODIMENT

The preferred embodiments of the present invention will be described hereinafter with reference to the attached drawings.

Example 1

Synthesis of 2-trimethylsilyl-2-propanol

To methyl lithium (100 mL, 1.4M, 140 mmol) in ether solution, acetyltrimethylsilane (18 mL, 127 mmol) is added dropwise using a syringe at 0° C. for an hour. The product is neutralized with saturated ammonium chloride solution. Organic layer is washed with distilled water several times and is dried with potassium carbonate. Pure 2-trimethylsilyl-2-propanol is obtained by distillation. Yield: 120 g (73%). b.p. 44° C. (33 mmHg).

Spectroscopic analysis by the NMR method is as follows:
$^1$H-NMR (CDCl$_3$): 0.02(9H, s, Si(CH$_3$)$_3$), 1.1(1H, s, OH), 1.18(6H, s, O—C(CH$_3$)$_2$—Si).

Example 2

Synthesis of 1,1-bis(trimethylsilyl)ethanol

Trimethylchlorosilane (20.5 g, 190 mmol) is dissolved in 30 mL of tetrahydrofuran. The solution is suspended with sodium (6.50 g, 283 mmol) and then refluxed at 80° C. Under the argon atmosphere, trimethylsilylacetate (3.12 g, 23.6 mmol) in 20 mL of tetrahydrofuran is added via a syringe for an hour and then the solution is refluxed for another 30 minutes. Then, precipitated inorganic residue is filtered and solvent is removed under vacuum. Remained oil is separated by vacuum distillation to give 1,1-bis(trimethylsilyl)ethanol (yield: 55%). b.p. 110° C. (24 mmHg).

1.5 mL of 6N HCl in 50 mL of dioxane is added to the above product at room temperature. The solution is neutralized with sodium bicarbonate. The product is extracted with ether which is then removed under vacuum. 1,1-bis(trimethylsilyl)ethanol is obtained by distillation (yield: 87%). b.p. 127° C. (32 mmHg).

Example 3

Synthesis of 2-(2-trimethylsilyl-2-propyl)carbonyloxy-5-norbornene 25 g (0.2 mol) of 2-trimethylsilyl-2-propanol prepared in Example 1 is dissolved in 200 mL of tetrahydrofuran in 500 mL of three neck round bottomed flask. The solution is cooled down to 0° C. and then n-BuLi (1.5M, 0.22 mol) is added dropwise. The solution is warm to room temperature and is stirred for 30 minutes and then cooled down to 0° C. 36 g (0.22 mol) of 2-chlorocarbonyl-5-norbornene prepared by Diels-Alder reaction of cyclopentadiene and acryloylchloride is diluted with purified 50 mL of tetrahydroifuran. The diluted solution is added to the reaction mixture through a dropping funnel, which is then warmed to room temperature and is stirred for another 6 hours to complete the reaction.

Figure 1:
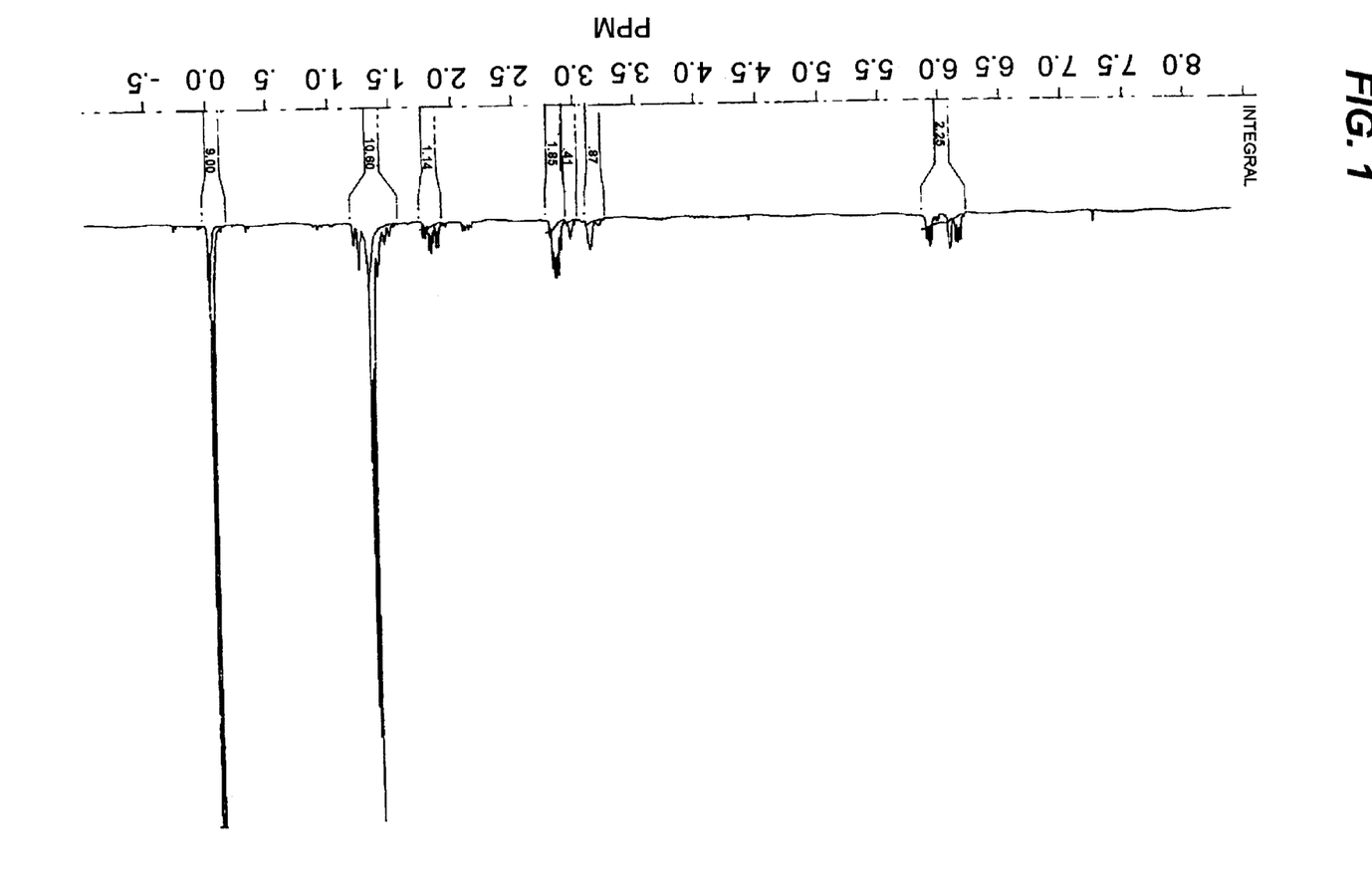
FIG. 1 is a $^1$H-NMR spectrum of 2-(2-trimethylsilyl-2-propyl)carbonyloxy-5-norbornene.
Figure 2:
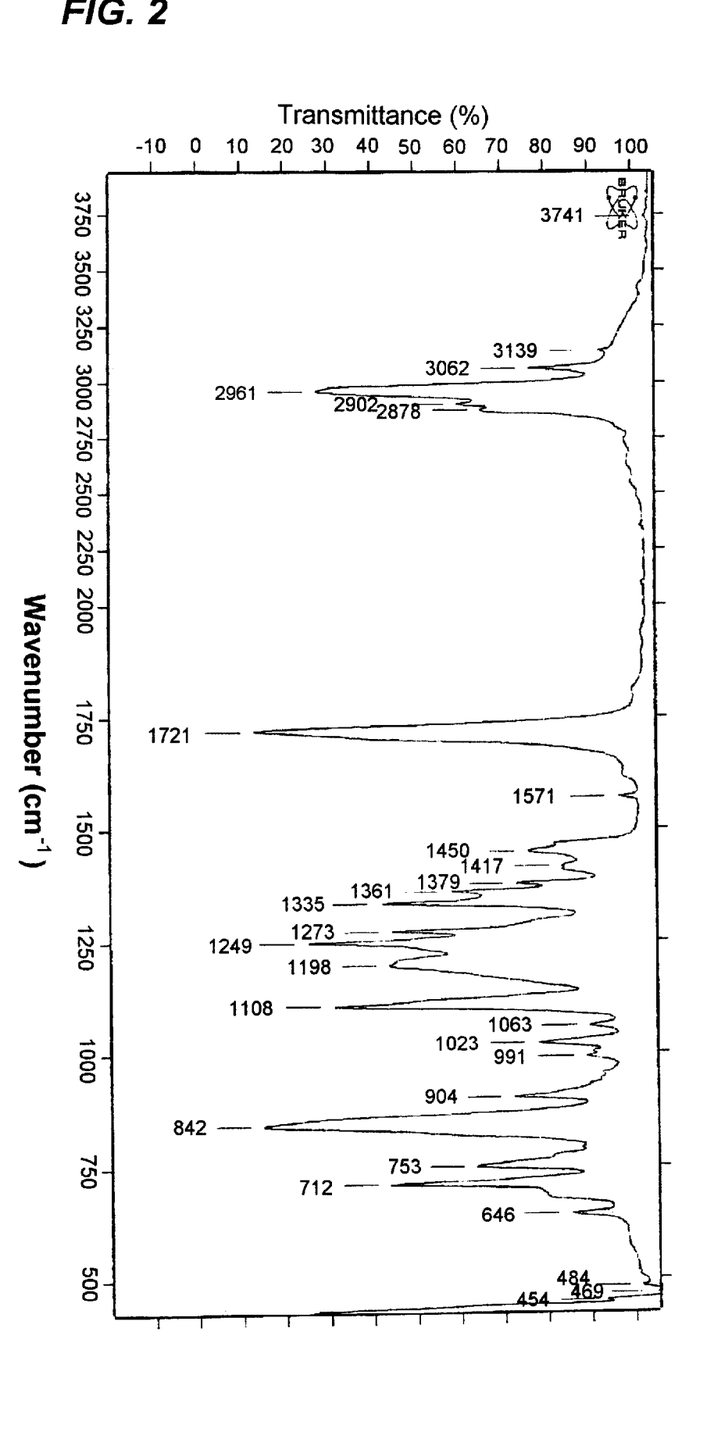
FIG. 2 is a FT-IR spectrum of 2-(2-trimethylsilyl-2-propyl)carbonyloxy-5-norbornene.

After the reaction, the reaction mixture is concentrated with rotary evaporator, the product is extracted with 400 mL of ethylether and 100 mL of sodium bicarbonate, and the organic layer is separated. The solution is washed with 300 mL of water and is then dried with 20 g of anhydrous magnesium sulfate by stirring at room temperature for 12 hours. The anhydrous magnesium sulfate is separated from the organic layer by a glass filter. The organic layer is concentrated with rotary evaporator. The concentrated liquid is distilled under vacuum to give 38. 4 g of pure 2-(2-trimethylsilyl-2-propyl)carbonyloxy-5-norbornene (yield: 76%). b.p. 58° C. (0.02 mmHg). The $^1$H-NMR spectrum in FIG. 1 and FT-IR spectrum in FIG. 2 showed the synthesis of desired product.

Spectroscopic analysis by the NMR and IR methods are as follows:
$^1$H-NMR (CDCl$_3$): 0.06(9H, s, Si(CH$_3$)$_3$), 1.4(6H, s, O—C(CH$_3$)$_2$—Si), 1.2–2.0(4H, m), 2.7–3.3(3H, m), 5.89–6.13(2H, m, endo-olefinic proton, exo-olefinic proton).

FT-IR(cm$^{-1}$): 2940(alicyclic CH), 1721(C=O of ester), 842(Si(CH$_3$)$_3$).

Example 4

Synthesis of 2-(1,1-bis(trimethylsilyl)ethyl) carbonyloxy-5-norbornene 35.8 g (0.188 mol) of 1,1-bis(trimethylsilyl)ethanol prepared in Example 2 is dissolved in 200 mL of tetrahydrofuran in 500 mL of three neck round bottomed flask. The solution is cooled down to 0° C. and then n-BuLi (1.5M, 0.2 mol) is added dropwise. The solution is warm to room temperature and is stirred for 30 minutes and then cooled down to 0° C. 29.5 g (0.188 mol) of 2-chlorocarbonyl-5-norbornene prepared by Diels-Alder reaction of cyclopentadiene and acryloylchloride is diluted with purified 50 mL of tetrahydroifuran. The diluted solution is added to the reaction mixture through a dropping funnel, which is then warmed to room temperature and is stirred for another 6 hours to complete the reaction.

Figure 3:
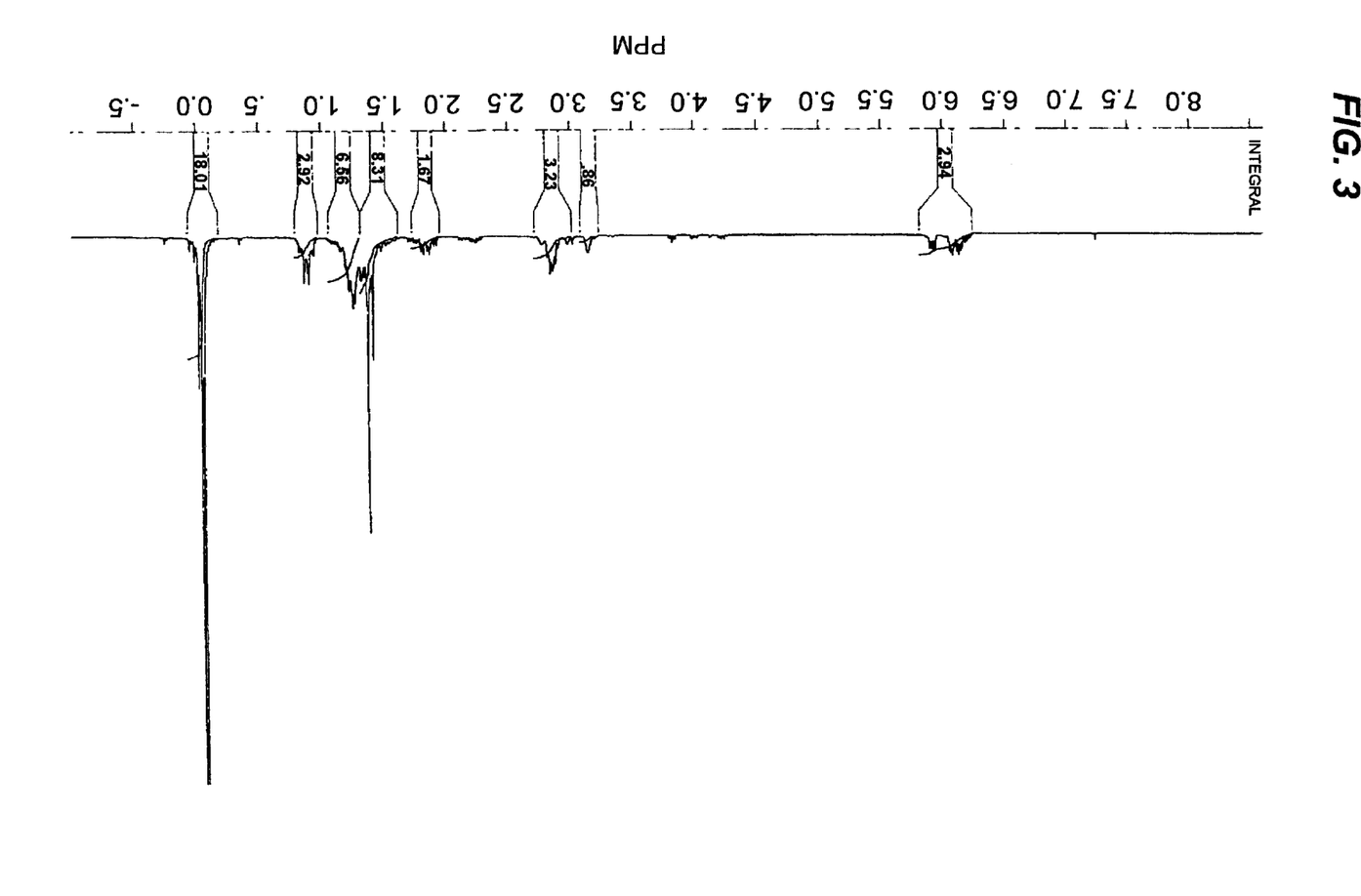
FIG. 3 is a $^1$H-NMR spectrum of 2-(1,1-bis(trimethylsilyl)ethyl)carbonyloxy -5-norbornene.
Figure 4:
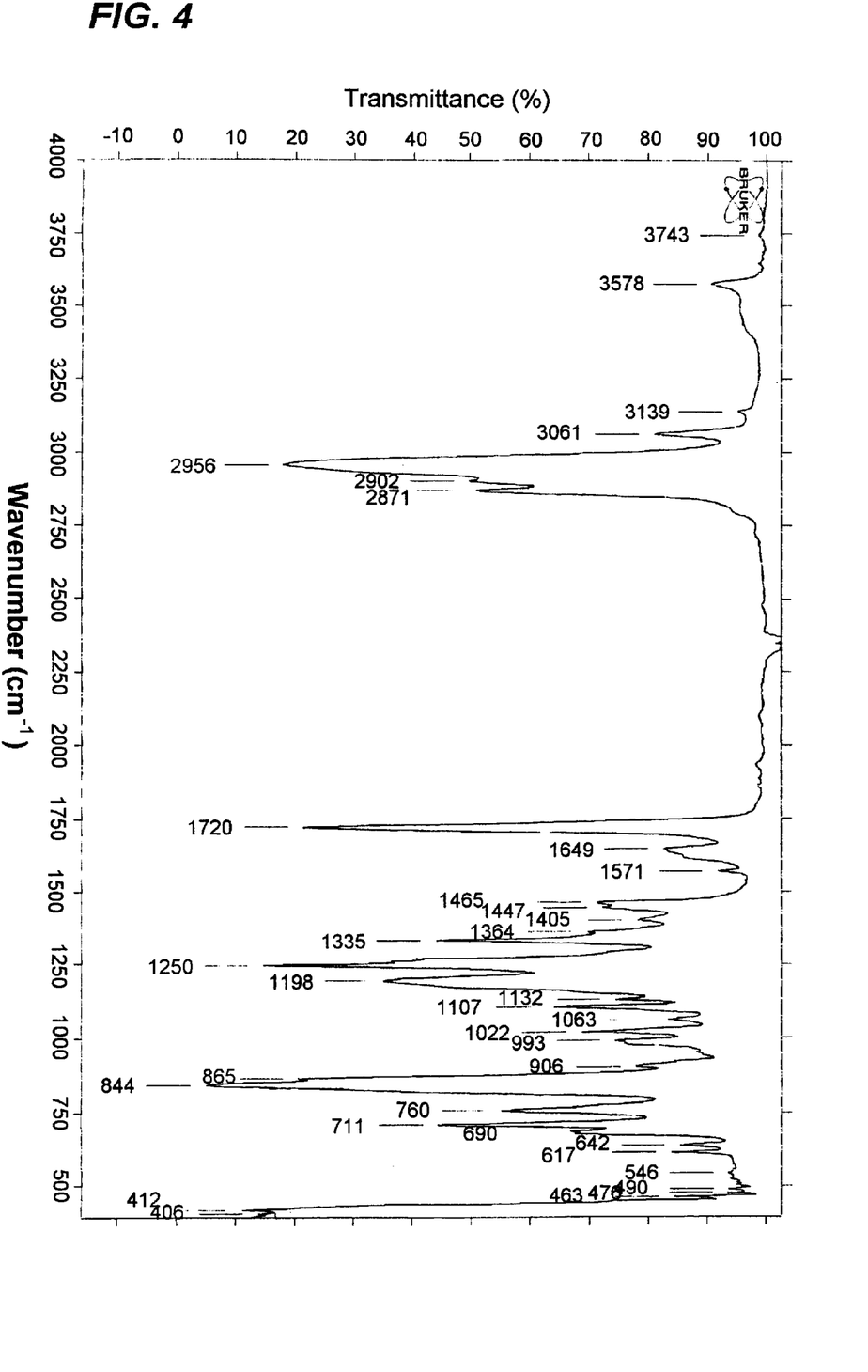
FIG. 4 is a FT-IR spectrum of 2-(1,1-bis(trimethylsilyl)ethyl)carbonyloxy-5-norbornene.

After the reaction, the reaction mixture is concentrated with rotary evaporator, the product is extracted with 400 mL of ethylether and 100 mL of sodium bicarbonate, and the organic layer is separated. The solution is washed with 300 mL of water and is then dried with 20 g of anhydrous magnesium sulfate by stirring at room temperature for 12 hours. The anhydrous magnesium sulfate is separated from the organic layer by a glass filter. The organic layer is concentrated with rotary evaporator. The concentrated liquid is distilled under vacuum to give 42.0 g of pure 2-(1,1-bis (trimethylsilyl)ethyl)carbonyloxy-5-norbornene (yield: 72%). b.p. 88° C. (0.02 mmHg). The $^1$H-NMR spectrum in FIG. 3 and FT-IR spectrum in FIG. 4 showed the synthesis of desired product.

Spectroscopic analysis by the NMR and IR methods are as follows:

$^1$H-NMR (CDCl$_3$): 0.06(18H, s, Si(CH$_3$)$_3$), 1.4(3H, O—C (CH$_3$)$_2$—Si), 1.2–2.0(4H, m), 2.7–3.3(3H, m), 5.89–6.13 (2H, m, endo-olefinic proton, exo-olefine proton).

FT-IR(cm$^{-1}$): 2940(alicyclic CH), 1720(C=O of ester), 844(Si(CH$_3$)$_3$).

Example 5

Figure 5:
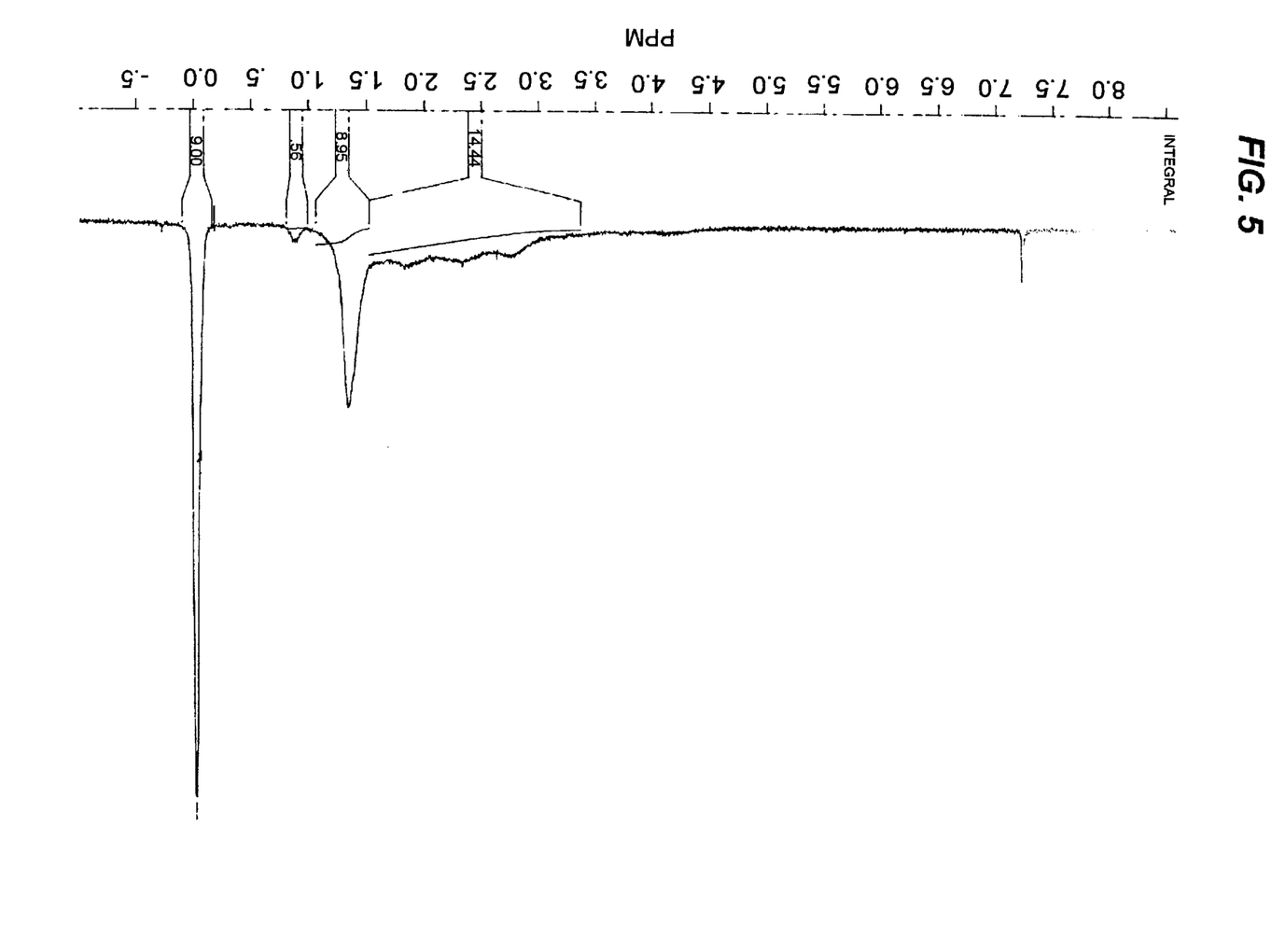
FIG. 5 is a $^1$H-NMR spectrum of 2-(2-trimethylsilyl-2-propyl)carbonyloxy-5-norbornene-maleic anhydride polymer.
Figure 6:
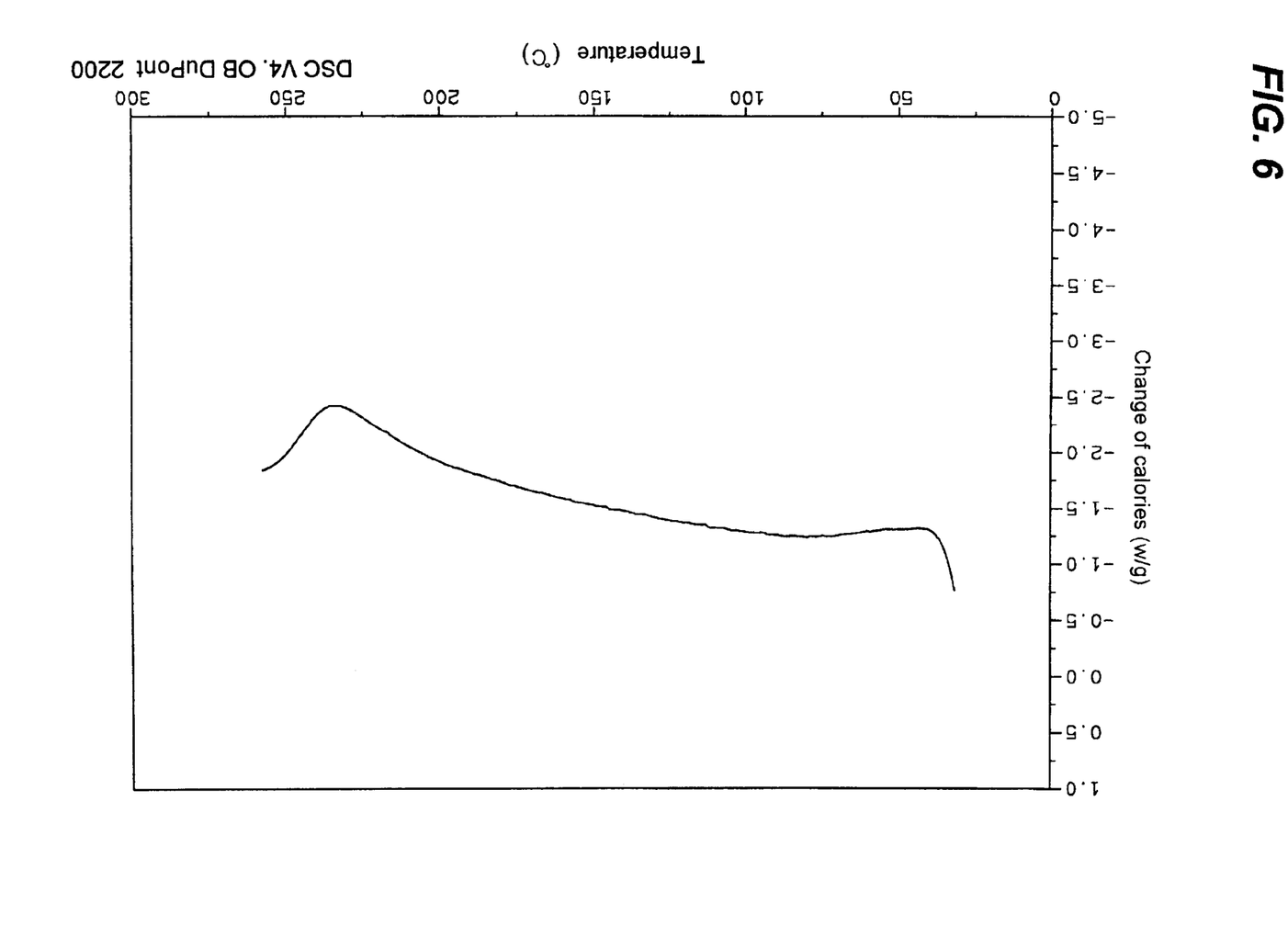
FIG. 6 is a DSC diagram of 2-(2-trimethylsilyl-2-propyl)carbonyloxy-5-norbornene-maleic anhydride polymer.

Synthesis of copolymer of 2-(2-trimethylsilyl-2-propyl) carbonyloxy-5-norbornene and maleic anhydride 2.57 g (0.01 mol) of 2-(2-trimethylsilyl-2-propyl) carbonyloxy-5-norbornene obtained in Example 3, 1.0 g (0.01 mol) of purified maleic anhydride and 0.033 g (1 mole %) 2,2-azobisisobutyronitrile as a radical initiator are added to a polymerization flask. The mixture is dissolved in 3.5 g of purified tetrahydrofuran and is polymerized at 65° C. for 24 hours under nitrogen atmosphere. After the polymerization, polymerization product is precipitated with mixed solvent of petroleum ether/ethylether (3/1 volume ratio), is saved by a glass filter, and is then dried at 40° C. for 12 hours to give 1.07 g of copolymer 2-(2-trimethylsilyl-2-propyl)carbonyloxy -5-norbornene and maleic anhydride (yield 30%) as a white solid. M$_n$ is 6,700 and glass transition temperature is not observed. The $^1$H-NMR spectrum in FIG. 5 showed the synthesis of a copolymer with desired structure. The glass transition temperature is identified by DSC and is presented in FIG. 6.

Example 6

Figure 7:
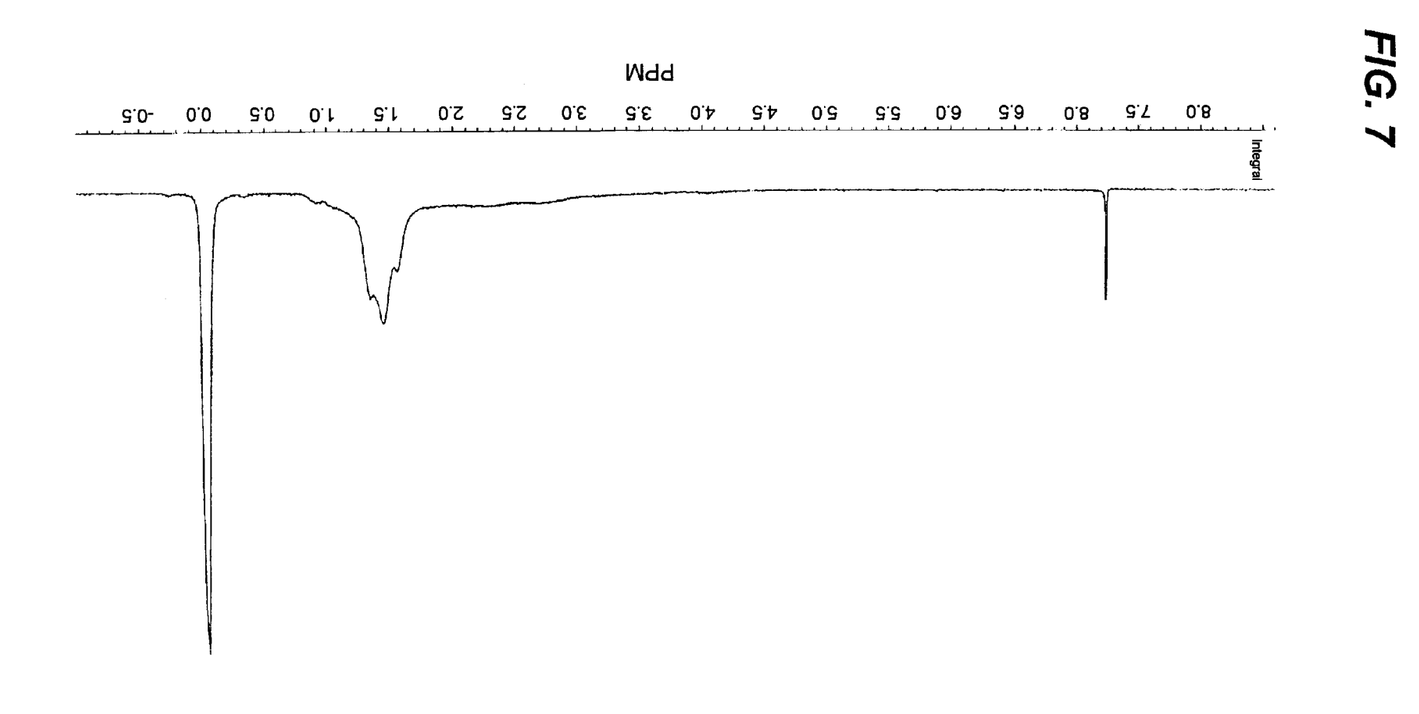
FIG. 7 is a $^1$H-NMR spectrum of 2-(2-trimethylsilyl-2-propyl)carbonyloxy-5-norbornene-maleic anhydride -2(2-trimethylsilyl-2-propyl)methacrylate polymer.

Synthesis of copolymer of 2-(2-trimethylsilyl-2-propyl) carbonyloxy-5-norbornene, maleic anhydride, and (2-trimethylsilyl-2-propyl) methacrylate 2.57 g (0.01 mol) of 2-(2-trimethylsilyl-2-propyl) carbonyloxy-5-norbornene obtained in Example 3, 1.0 g (0.01 mol) of purified maleic anhydride, 1.36 g (0.006 mol) of (2-trimethylsilyl-2-propyl)methacrylate, and 0.067 g (1.5 mole %) 2,2-azobisisobutyronitrile as a radical initiator are added to a polymerization flask. The mixture is dissolved in 3.2 g of purified tetrahydrofuran and is polymerized at 65° C. for 24 hours under nitrogen atmosphere. After the polymerization, polymerization product is precipitated with methanol, is saved by a glass filter, and is then dried at 40° C. for 12 hours to give 2.47 g of copolymer 2-(2-trimethylsilyl-2-propyl)carbonyloxy -5-norbornene-maleic anhydride-(2-trimethylsilyl-2-propyl)methacrylate (yield 50%) as a white solid. M$_n$ is 6,520 and glass transition temperature is not observed. The $^1$H-NMR spectrum in FIG. 7 showed the synthesis of a copolymer with desired structure.

Example 7

Manufacture of Photoresist and Formation of Photoresist Pattern

In a lab protected from deep-UV light, 0.2 g of copolymer of 2-(2-trimethylsilyl-2-propyl)carbonyloxy-5-norbornene-maleic anhydride and 0.004 g of triphenylsulfonium triflate as a photosensitive acid generator are dissolved in 1.4 g of propyleneglycolmonomethyletheracetate. The solution is filtered with 0.2 μm of syringe filter to make a photoresist solution.

Figure 8:
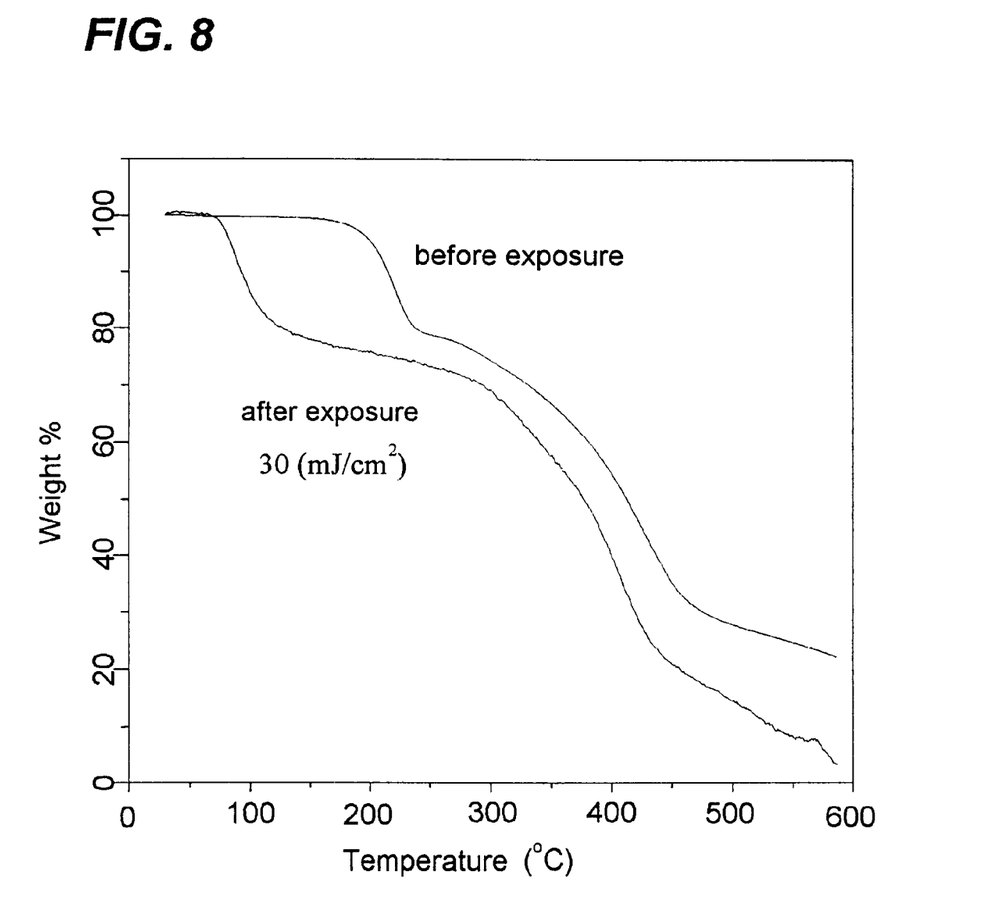
FIG. 8 is a thermogravimetric analysis result of photoresist containing 2-(2-trimethylsilyl-2-propyl)carbonyloxy-5-norbornene-maleic anhydride polymer.

Hexamethyldisilazane is dropped on a silicon wafer. The wafer is pre-treated by spin-coating at the speed of 1500 rpm. Then the photoresist solution prepared above is dropped on the silicon wafer and spin-coated at the speed of 2500 rpm to give a thin film of photoresist with thickness of 0.4 μm. The coated silicon wafer is cut in half. Deep-UV with 30 mJ/cm$^2$ is irradiated on one of the two, while the other is not irradiated. FIG. 8 shows the thermogravimetric analysis (TGA) result of the photoresist films scraped from each sample. FIG. 8 shows that when acid is not generated the decomposition of 2-trimethylsilyl-2-propyl functional group begins at 195° C., but when acid is generated decomposition begins at 76° C.

The photoresist solution is coated on a silicon wafer according to the above condition, is soft-baked at 120° C. for 90 seconds, light with 30 mJ/cm$^2$ is irradiated through a mask, and baking at 130° C. for 90 seconds to provide a clear latent image. The etching of the image with reactive ion etching apparatus generating oxygen plasma (O$_2$ plasma, flow rate: 50 sccm, pressure: 50 mtorr, power: 50 W) to give different silicon content between the exposed area and unexposed area due to decomposition of silicon containing side chain by the photosensitive acid on the exposed area. The etching speed on the unexposed area dropped due to SiOx layer resulting from remained silicon content. In this way, line/space pattern with 0.2 micron can be obtained by a contact printing.

Example 8

Manufacture of Photoresist and Formation of Photoresist Pattern

In a lab protected from deep-UV light, 0.2 g of copolymer of 2-(2-trimethylsilyl-2-propyl)carbonyloxy-5-norbornene-maleic anhydride-(2-trimethylsilyl-2-propyl)methacrylate and 0.004 g of triphenylsulfonium triflate as a photosensitive acid generator are dissolved in 1.4 g of propyleneglycolmonomethyletheracetate. The solution is filtered with 0.2 μm of syringe filter to make a photoresist solution.

Hexamethyldisilazane is dropped on a silicon wafer. The wafer is pre-treated by spin-coating at the speed of 1500 rpm. Then the photoresist solution prepared above is dropped on the silicon wafer and spin-coated at the speed of 2500 rpm to give a thin film of photoresist with thickness of 0.4 μm. The coated silicon wafer is cut in half.

The wafer is soft-baked at 120° C. for 90 seconds, is irradiated with 30 mJ/cm² light through a mask, and is baked at 130° C. for 90 seconds to provide a clear latent image. The etching of the image with reactive ion etching apparatus generating oxygen plasma (O₂ plasma, flow rate:50 sccm, pressure: 50 mtorr, power: 50 W) causes difference in the etching speed between the exposed area and unexposed area as shown in Example 7 and allows dry developing. In this way, line/space pattern with 0.2 micron can be obtained by a contact printing.

Example 9

Manufacture of Photoresist and Formation of Photoresist Pattern

In a lab protected from deep-UV light, hexamethyldisilazane is dropped on a silicon wafer and spin-coats the wafer at the speed of 1500 rpm for a pre-treatment. Then Novolac resist is spin-coated with thickness of 0.4 μm as a sublayer of double layer resist, and is baked at 120° C. for 90 seconds. To the wafer coated with Novolac, photoresist solution of 2-(2-trimethylsilyl-2-propyl)carbonyloxy-5-norbornene-maleic anhydride polymer prepared in Example 8 is dropped and spin-coats at the speed of 3500 rpm to provide a thin film imaging layer for Novolac layer with thickness of 0.2 μm.

The coated resist is soft-baked at 120° C. for 90 seconds, is irradiated with 30 mJ/cm² light through a mask, and is baked at 130° C. for 90 seconds to provide a clear latent image. It is developed with 2.38 wt % of aqueous tetramethyl ammonium hydroxide solution and is etched with reactive ion etching apparatus generating oxygen plasma (O₂ plasma, flow rate: 50 sccm, pressure: 50 mtorr, power: 50 W). This process causes the exposed area to be etched whereas the unexposed area is not etched due to the formation of SiOx film resulting from silicon component as shown in Example 7. In this way, line/space pattern with 0.2 micron can be obtained by a contact printing.

Example 10

Manufacture of Photoresist and Formation of Photoresist Pattern

In a lab protected from deep-UV light, hexamethyldisilazane is dropped on a silicon wafer and spin-coats it at the speed of 1500 rpm for a pre-treatment. Then Novolac resist is spin-coated with thickness of 0.4 μm as a sublayer of double layer resist, and is baked at 120° C. for 90 seconds. To the wafer coated with Novolac, photoresist solution of 2-(2-trimethylsilyl-2-propyl)carbonyloxy-5-norbornene-maleic anhydride-(2-trimethylsilyl-2-propyl)methacrylate polymer prepared in Example 8 is dropped and spin-coats at the speed of 3500 rpm to provide a thin film imaging layer for Novolac layer with thickness of 0.2 μm.

The coated resist is soft-baked at 120° C. for 90 seconds, is irradiated with 30 mJ/cm² light through a mask, and is baked at 130° C. for 90 seconds to provide a clear latent image. It is developed with 2.38 wt % of aqueous tetramethyl ammonium hydroxide solution and is etched with reactive ion etching apparatus generating oxygen plasma (O₂ plasma, flow rate: 50 sccm, pressure: 50 mtorr, power: 50 W). This process causes the exposed area to be etched whereas the unexposed area is not etched due to the formation of SiOx film resulting from silicon component as shown in Example 7. In this way, line/space pattern with 0.2 micron can be obtained by a contact printing.

As explained above, unlike existing polymers for photoresist matrix, polymers made by norbornene monomers containing organometal described in the present invention is a chemical amplification type induced by photosensitive acids and can result in difference in silicon content between the exposed area and unexposed area due to dissociation of side chain containing silicon. The difference in the silicon content results in difference in etching speed under oxygen plasma, which makes dry developing possible.

The application of photoresist according to the present invention to fine processing technology provides superior sensitivity, and prevents deformation and collapse of patterns according to the increase of aspect ratio of pattern. In addition, compared to resist using oxygen plasma after silylation or wet developing such as silylation or multilayer resist systems, the process according to the present invention is much simple and solvent is not used, so that it is economically favorable.

Furthermore, the photoresist according to the present invention has different silicon content depending on exposure and baking and changes polarity so that wet developing is possible and can be used as an upper layer of double layer resist system.

The present invention is about a resist with a novel concept which not just modifies existing materials or improves problems but can overcome limits of existing wet developing type photoresist. In the application of field process, it can be continuously applied by just changing gas, so the process is simple, reduces pollution and provides economical advantages.

Although the present invention has been illustrated with reference to embodiments of the present invention, various modifications are possible within the scope of the present invention by a person skilled in the art. Therefore, the scope of the present invention should be defined not by the illustrated embodiments but by the attached claims.

What is claimed is:

1. A norbornene monomer used for photoresist represented by the following Formula (I), wherein $R_1$ to $R_8$ independently represent hydrogen, alkyls having from 1 to 4 carbon atoms, alkoxy having from 1 to 4 carbon atoms, phenyl or —$MR'_3$; M is either Si, Ge, Sn or OSi; and R' is either alkyl having from 1 to 4 carbon atoms, alkoxy having from 1 to 4 carbon atoms, phenyl, benzyl or phenoxy.

2. A photoresist comprising a polymer and a photosensitive acid generator as shown in the following Formula (III), (III)

wherein $R_1$ to $R_8$ independently represent hydrogen, alkyls having from 1 to 4 carbon atoms, alkoxy having from 1 to 4 carbon atoms, phenyl or —$MR'_3$; M is either Si, Ge, Sn or OSi; and R' is either alkyl having from 1 to 4 carbon atoms, alkoxy having from 1 to 4 carbon atoms, phenyl, benzyl or phenoxy; n is degree of polymerization and is between 1 to 100.

3. A method of forming a photoresist pattern using the photoresist of claim 2, said method comprising the steps of:

forming a photoresist film by coating photoresist on a substrate;

exposing said photoresist film through an exposure mask;

baking the exposed resultant; and selectively etching the exposed area in said photoresist film by a reactive ion etching utilizing oxygen plasma.

4. The method of claim 3, wherein the baking step is performed at 90~140° C.

5. A photoresist comprising a polymer and a photosensitive acid generator as shown in the following Formula (VI), (VI)

wherein, A represents the following Formula (VII) or (VIII), (VII)

(VIII)

and B represents the following Formula (IX), (X) or (XI), (IX)

(X)

(XI)

wherein $R_1$ to $R_{10}$ independently represent hydrogen, alkyls having from 1 to 4 carbon atoms, alkoxy having from 1 to 4 carbon atoms, phenyl or —$MR'_3$; M is either Si, Ge, Sn or OSi; and R' is either alkyl having from 1 to 4 carbon atoms, alkoxy having from 1 to 4 carbon atoms, phenyl, benzyl or phenoxy; $R_{11}$, to $R_{13}$ independently represent hydrogen or alkyl; x,y,z are mole ratio of a polymer and x+y+z=1.

6. A photoresist manufacturing method, comprising the steps of: forming polymer either polymerizing the norbornenes represented in the above Formula (I) according to claim 1, copolymerizing norbornenes with maleic anhydride, or polymerizing by mixing silicon-containing acrylate or methacrylate monomer as well as maleic anhydride with norbornene monomers; and dissolving said polymer and photosensitive acid generator in solvent.

7. A method of forming a photoresist pattern using the photoresist of claim 5, said method comprising the steps of:

forming a photoresist film by coating photoresist on a substrate;

exposing said photoresist film through an exposure mask;

baking the exposed resultant; and selectively etching the exposed area in said photoresist film by a reactive ion etching utilizing oxygen plasma.

8. The method of claim 7, wherein the baking step is performed at 90~140° C.

* * * * *